/ United States Patent / Lin et al.

(10) Patent No.: US 12,330,119 B2
(45) Date of Patent: *Jun. 17, 2025

(54) DUST AND SPLASH-PROOF FILTER (71) Applicant: Honeywell International Inc., Charlotte, NC (US)

(72) Inventors: Qidao Lin, Charlotte, NC (US); Feng Liang, Charlotte, NC (US); Yong Tang, Charlotte, NC (US)

(73) Assignee: Honeywell International Inc., Charlotte, NC (US)

( * ) Notice: Subject to any disclaimer, the term of this patent is extended or adjusted under 35 U.S.C. 154(b) by 569 days.

This patent is subject to a terminal disclaimer.

(21) Appl. No.: 17/582,657

(22) Filed: Jan. 24, 2022

(65) Prior Publication Data

US 2022/0143559 A1 May 12, 2022

Related U.S. Application Data (63) Continuation of application No. 16/336,970, filed as application No. PCT/CN2016/101429 on Oct. 5, 2016, now Pat. No. 11,266,954.

(51) Int. Cl.
*B01D 63/08* (2006.01)
*B01D 39/16* (2006.01)
(Continued)

(52) U.S. Cl.
CPC ......... *B01D 63/08* (2013.01); *B01D 39/1623* (2013.01); *B01D 46/543* (2013.01); *B01D 53/228* (2013.01); *B01D 53/265* (2013.01); *B01D 53/268* (2013.01); *B01D 63/00* (2013.01); *B01D 63/082* (2013.01); *B01D 69/02* (2013.01); *B01D 69/06* (2013.01); *B01D 71/261* (2022.08); *B01D 71/36* (2013.01);
(Continued)

(58) Field of Classification Search
None
See application file for complete search history.

(56) References Cited

U.S. PATENT DOCUMENTS 767,859 A * 8/1904 Ballance et al. ... B01D 46/0004
55/502
4,633,704 A 1/1987 Tantram et al.
(Continued)

FOREIGN PATENT DOCUMENTS

CN 101275923 A 10/2008
CN 101363818 A 2/2009
(Continued)

OTHER PUBLICATIONS

CN Office Action Mailed on Apr. 18, 2024 for CN Application No. 202210782770, 3 page(s).
(Continued)

*Primary Examiner* — Jason M Greene
(74) *Attorney, Agent, or Firm* — Alston & Bird LLP (57) ABSTRACT

Embodiments relate generally to a filter, for example, for attachment onto a gas detector device or a gas sensor, and attempt to improve the efficiency and service life of the filter. Embodiments typically comprise a dustproof membrane and a waterproof membrane. Some embodiments may also comprise a splash-proof cap and/or features to reduce negative pressure on the filters.

15 Claims, 5 Drawing Sheets (51) Int. Cl.

| | | |
|---|---|---|
| *B01D 46/54* | (2006.01) | |
| *B01D 53/22* | (2006.01) | |
| *B01D 53/26* | (2006.01) | |
| *B01D 63/00* | (2006.01) | |
| *B01D 69/02* | (2006.01) | |
| *B01D 69/06* | (2006.01) | |
| *B01D 71/26* | (2006.01) | |
| *B01D 71/36* | (2006.01) | |
| *G01N 33/00* | (2006.01) | |

(52) U.S. Cl.
CPC ... *G01N 33/0009* (2013.01); *B01D 2053/221* (2013.01); *B01D 2239/0618* (2013.01); *B01D 2313/08* (2013.01); *B01D 2313/14* (2013.01); *B01D 2313/206* (2022.08); *B01D 2313/21* (2013.01); *B01D 2313/23* (2013.01); *B01D 2319/025* (2013.01); *B01D 2319/06* (2013.01); *B01D 2325/38* (2013.01); *G01N 33/0011* (2013.01)

(56) References Cited

U.S. PATENT DOCUMENTS

| | | | |
|---|---|---|---|
| 5,582,907 | A | 12/1996 | Pall |
| 5,667,566 | A | 9/1997 | Flynn et al. |
| 5,914,154 | A * | 6/1999 | Nemser .............. B01D 39/1623 427/244 |
| 11,266,954 | B2 * | 3/2022 | Lin ..................... B01D 53/228 |
| 2006/0090645 | A1 | 5/2006 | Kent |
| 2011/0226053 | A1 | 9/2011 | Sorenson et al. |
| 2019/0232231 | A1 | 8/2019 | Lin et al. |

FOREIGN PATENT DOCUMENTS

| | | |
|---|---|---|
| CN | 202355944 U | 8/2012 |
| CN | 204556484 U | 8/2015 |
| CN | 105569778 A | 5/2016 |
| CN | 109789366 A | 5/2019 |
| DE | 102004036941 A1 | 3/2006 |
| DE | 102011111479 A1 | 2/2013 |
| JP | 2005-201860 A | 7/2005 |
| JP | 2008-051627 A | 3/2008 |
| JP | 2016-166820 A | 9/2016 |

OTHER PUBLICATIONS

English Translation of CN Office Action dated Apr. 18, 2024 for CN Application No. 202210782770, 4 page(s).
CN Notice of Allowance Mailed on Apr. 20, 2022 for CN Application No. 201680089615.
English Translation of CN Office Action Mailed on Apr. 20, 2022 for CN Application No. 201680089615.
Notice of Allowance and Fees Due (PTOL-85) Mailed on Feb. 4, 2022 for U.S. Appl. No. 16/336,970.
CN Office Action Mailed on Jun. 26, 2024 for CN Application No. 202210782770, 5 page(s).
English Translation of CN Office Action dated Jun. 26, 2024 for CN Application No. 202210782770, 7 page(s).
CN Office Action Mailed on Aug. 18, 2023 for CN Application No. 202210782770, 9 page(s).
English Translation of CN Office Action dated Aug. 18, 2023 for CN Application No. 202210782770, 4 page(s).
English translation of CN Search report dated Aug. 18, 2023 for CN Application No. 202210782770, 3 page(s).
English language machine translation for DE 102004036941 A1. Retrieved from translationportal.epo.org on Mar. 15, 2021. (Year: 2021).
English language machine translation for JP 2005-201860. Retrieved from translationportal.epo.org on Mar. 15, 2021. (Year: 2021).
Final Office Action received for U.S. Appl. No. 16/336,970, mailed on Aug. 18, 2021, 12 pages.
International Search and Written Opinion for Application No. PCT/CN2016/101429, dated Jun. 15, 2017, 9 pages.
Non-Final Rejection Mailed on Mar. 22, 2021 for U.S. Appl. No. 16/336,970.
Notice of Allowance received for U.S. Appl. No. 16/336,970, mailed on Feb. 4, 2022, 4 pages.
Office Action issued in Chinese Application No. 201680089615.3 on Jan. 26, 2021, 21 pages.
Office Action issued in Chinese Application No. 201680089615.3 on Nov. 10, 2021, 8 pages.
Notice of Allowance and Fees Due (PTOL-85) Mailed on Oct. 29, 2021 for U.S. Appl. No. 16/336,970, 7 page(s).
CN Notice of Allowance Mailed on Dec. 1, 2024 for CN Application No. 202210782770, 4 page(s).
English translation of CN Notice of Allowance dated Dec. 1, 2024 for CN Application No. 202210782770, 2 page(s).

* cited by examiner

DUST AND SPLASH-PROOF FILTER

CROSS-REFERENCE TO RELATED APPLICATIONS

The present application is a continuation of U.S. application Ser. No. 16/336,970, filed Mar. 27, 2019, which application claims priority to International Patent Application No. PCT/CN2016/101429, filed Oct. 5, 2016, the contents of which applications are herein incorporated by reference in their entirety,

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments generally relate to filtration of air intake, for example, with regards to gas detector or gas sensor devices.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or "approximately" or the like, when used with a number, may mean that specific number, or alternatively, a range in proximity to the specific number, as understood by persons of skill in the art field (for example, +/−10%); and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The embodiments of the disclosure typically relate to a filter configured to attach to a gas detector or a gas sensor. Due to varying ambient conditions, gas detectors generally may not provide accurate measurements using unfiltered air. For example, in dusty or moist environments the filters may either clog or lose effectiveness and, typically, cannot be effectively used outdoors. In another example, entry of large drops of water (for example, due to splashing) may compromise a filter. Furthermore, use of a single filter may negatively impact filter life, since dust and other particulates may interfere with such a filter's ability to block water without clogging. Additionally, if the amount of negative air pressure experienced by the filter is too high, water saturation/seepage may be a problem. Embodiments of the present invention may address one or more of such issues in an attempt to provide enhanced filtration of air for gas detectors/sensors or other such devices with air intake.

Disclosed embodiments relate to a filter (for example, for filtering input air flow to remove dust, particulates, and/or moisture), which might, for example, be used for the air input of a gas sensor or detector. Typically, disclosed filter embodiments would include two separate filtration membranes. For example, a dustproof membrane and a waterproof membrane positioned to operate in series (for example, with the dustproof membrane being located upstream of the waterproof membrane (such that air would first flow through the dustproof membrane before passing through the waterproof membrane) (although other configurations (such as the waterproof membrane being upstream of the dustproof membrane) may also be included within the scope of this disclosure)). Typically, the two filtration membranes would be located within a housing (which typically encloses the two filtration membranes and, generally, includes an inlet and an outlet for directing air through the filtration membranes and out to the air inlet (for example, for a gas detector or gas sensor or other sensor requiring an air input). Additionally, for manufacturing purposes, the housing may be two separate elements which can be joined together around the two filtration elements. Thus, disclosed filter embodiments would typically comprise: a top housing, having at least one outlet aperture; a bottom housing, having one or more inlet apertures; a dustproof membrane; and a waterproof membrane (and as noted above, the dustproof membrane often would be located upstream of the waterproof membrane).

Typically, the two filtration membranes would be spaced apart (e.g. not contacting one another), for example with the dustproof membrane being spaced approximately 1, 2, 3, 1-3, 1-5, 2-3, 2-5, or 3-5 millimeters from the waterproof membrane. While persons of skill should appreciate the types of materials which would function effectively as a dustproof membrane and/or waterproof membrane, an exemplary dustproof membrane might comprise polypropylene nonwoven (PPNW) while an exemplary water-proof membrane might comprises polytetrafluoroethylene (PTFE). In some embodiments, each of the one or more inlet apertures would have an open diameter of approximately 6-7 millimeters (and typically there might be six such inlet apertures), while the outlet aperture would have an open surface area of approximately diameter of approximately 6 millimeters or less. In other words, the ratio of the size of the inlet apertures to the size of the outlet aperture might be approximately 6 to 1 or larger. By having a larger inlet aperture area compared to the outlet aperture area, the negative pressure on the filtration membranes may be reduced, which, for example, may reduce the risk of water seepage/saturation of the filtration membranes in a way that could negatively impact filter performance or life.

Some embodiments may have the waterproof membrane attached/affixed (typically in a permanent, sealing manner) to a top surface of the bottom housing. For example, such attachment may be by welding (for example, sonic welding). Embodiments may also optionally have a support frame located between the dustproof membrane and the waterproof membrane. For example, the dustproof membrane may be located below and in contact with the support frame. In some embodiments, the waterproof membrane may be spaced above the support frame. Typically, the support frame will be configured to allow airflow therethrough, so that air may flow through the dustproof membrane and then into the waterproof membrane without significant obstruction and/or turbulence. So, for example, in some embodiments the support frame might include one or more air flow apertures, with the one or more air flow apertures typically corresponding with (for example, sized similarly and/or positioned in alignment with) the one or more inlet apertures in the bottom housing.

Embodiments of the disclosed filter may also include features which the Applicant has found may protect the filtration elements from splashes and other large water intrusion. For example, the bottom housing may comprise a raised lip extending around the perimeter or circumference of the bottom surface of the bottom housing. Some embodiments may have (for example, either in conjunction with or instead of the raised lip around the perimeter of the bottom housing's bottom surface) a raised lip or edge or wall around the perimeter or circumference of each of the inlet apertures in the bottom housing of the filtration device. One or more embodiment may also include comprising a splash-proof cap, which might be a separate element which is either permanently affixed to the bottom housing or (more typically) which is removably affixed to the bottom housing of the filter. So, for example, the splash-proof cap would typically comprise a hollow body with a top open end configured for attachment onto the bottom housing.

The splash-proof cap is generally designed to shield the filter from splashes or other liquid water intrusions and/or to direct any water which does enter the filter (for example, either via splashes of liquid water or condensation from moist air which might condense, for example, at the waterproof membrane) outward. So, for example, the bottom surface of the hollow body typically would have one or more entry apertures, which would typically be located on the bottom surface of the hollow body (and, typically, the entry apertures might be sized similarly to and/or aligned with the inlet apertures on the bottom housing of the filtration device), and typically the bottom surface of the hollow body would be curved inward (e.g. curved to form a bowl-like shape which would direct any water entering the hollow body towards the center of the bottom surface of the hollow body of the splash-proof cap) with respect to the hollow body. Furthermore, the splash-proof cap typically would have one or more baffles, which would be configured with respect to the entry apertures of the splash-proof cap to block easy or direct entry of water through the entry apertures (beyond the point of the baffles) (while allowing airflow therethrough). While it could be possible to have a single baffle which is configured to shield all of the entry apertures (and this embodiment is included within the scope of this disclosure), more typically there would be one baffle for each entry aperture (e.g. direct or one-to-one correspondence). Regardless, the one or more baffles would typically correspond with the one or more entry apertures in the bottom surface.

Typically, each of the baffles would be aligned with the corresponding entry aperture (for example, positioned over the entry aperture and/or sharing a common vertical centerline). And while the baffles could be shaped and/or oriented in various ways configured to effectively block/shield water entry through the entry apertures, typical embodiments might have each baffle oriented generally parallel to the corresponding entry aperture and/or with each baffle sized to be at least as large as the corresponding entry aperture (although in some embodiments, the baffles could be slightly smaller in size than their corresponding entry aperture). The baffles are typically inset slightly in the hollow body of the splash-proof cap, such that they may effectively block/shield from entry of water while allowing airflow around the baffles via the inset. So, for example, each of the one or more baffles would typically be located within the hollow body of the splash-proof cap (e.g. within the hollow cavity of the splash-proof cap) and spaced approximately 3-4 millimeters from the corresponding entry aperture (e.g. inset approximately 3-4 millimeters from the bottom surface of the hollow body of the splash-proof cap). Typically, the entry apertures of the splash-proof cap would have an open surface area at least as great as that of the inlet apertures of the bottom housing.

In some embodiments, the bottom surface of the hollow body of the splash-proof cap might optionally include a raised lip (or wall extension or edge) around the perimeter/circumference thereof. Also, some embodiments might include (either alone or in conjunction with the perimeter raised lip) a raised lip (or wall or edge) around the perimeter of each of the entry apertures (such that the bottom surface of the hollow body of the splash-proof cap is inset from the actual openings of the entry apertures or such that the actual opening of the entry apertures projects or extends out (for example, downward) (for instance, like a tube for each entry aperture) from the bottom surface of the hollow body of the splash-proof cap). In some embodiments, one or more of the features of the splash-proof cap might instead be associated with the bottom housing of the filter (for example, the bottom surface of the bottom housing might be curved inward, there could be baffles corresponding to the inlet apertures of the bottom housing of the filter, and/or there could be a raised lip about the perimeter of the bottom housing and/or each of the inlet apertures similar to those described above with respect to the splash-proof cap).

Often, the splash-proof cap would be removably attached to the bottom housing. For example, the splash-proof cap might further comprise an elastomeric bumper on an inner surface of the hollow body, configured to allow press-fit attachment of the splash-proof cap to the bottom housing. Typically, the press-fit attachment would be sufficient to prevent entry of water and/or air (e.g. sealed) so that the only entryway to the filter (e.g. the inlet apertures of the bottom housing) would be through the entry apertures at the bottom of the splash-proof cap and/or would be sufficient to securely hold the splash-proof cap in place on the bottom housing (so it would not fall off during routine usage). Alternatively, the splash-proof cap might be screwed on (with corresponding screw threads on the bottom housing and the top of the splash-proof cap) or otherwise removably attached. And in some embodiments, the splash-proof cap could be permanently attached (for example via adhesive or welding) to the bottom housing. While persons of skill should understand the disclosed embodiments based on the above disclosure, the following figures may provide specific examples that may further clarify the disclosure.

Figure 1:
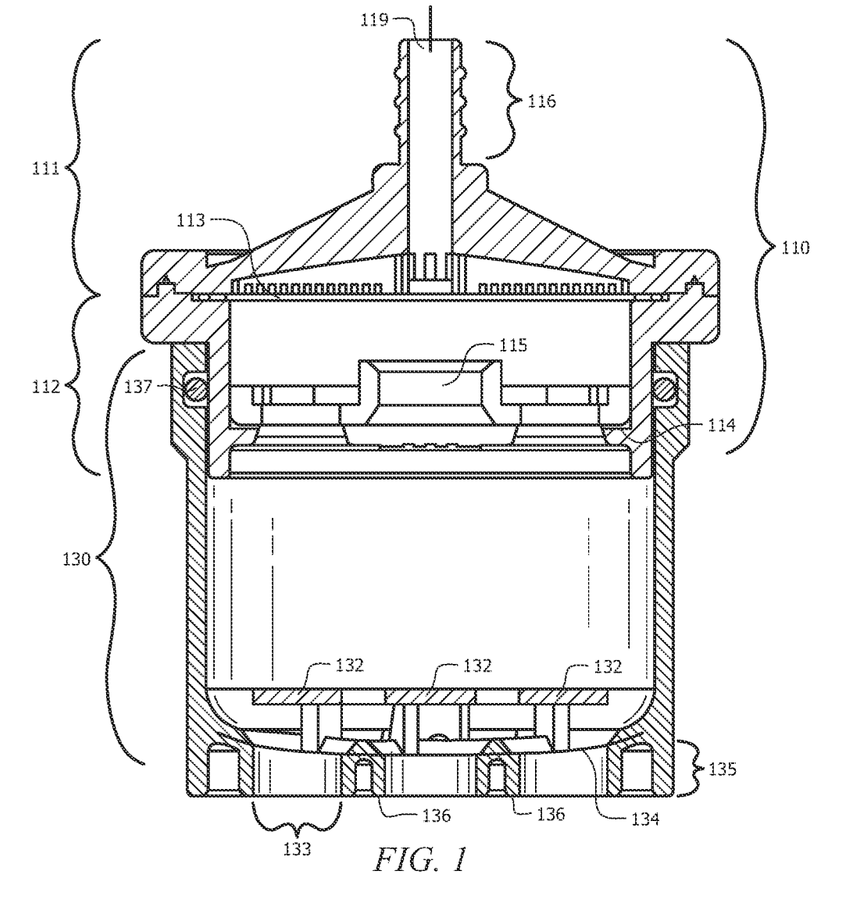
FIG. 1 illustrates a cross-sectional view of an exemplary embodiment of a filter and a splash-proof cap.

Turning now to the drawings, FIG. 1 illustrates an exemplary embodiment of a filter 110 comprising a top housing 111, a bottom housing 112, at least two filtering membranes, and, optionally, a splash-proof cap 130. The top housing 111 may comprise at least one outlet aperture 119 (typically approximately 6 millimeters or less in diameter) configured to attach snugly (for example, with flexible tubing), for example, to a gas detector. While the outlet apertures 119 may be located anywhere on the top housing 111 and be of any shape, in FIG. 1, the single outlet aperture 119 is located on the center axis (at the top housing 111) and is tubular in shape. The bottom housing 112 may be located upstream of the top housing 111 and may comprise one or more inlet apertures (each typically having a diameter of 6-7 millimeters). The inlet apertures may have a large enough open surface area to allow for a sufficient volume of air to flow through the filter 110, and, typically, the ratio of the open surface area of the outlet aperture 119 to the inlet aperture would be approximately, for example, 1 to 6 if there are 6 inlet apertures and one outlet aperture, as shown in FIG. 1 (which may reduce negative pressure effects on the membranes). Typically, the top and bottom housing (111, 112) may be welded together via supersonic welding to form a water-proof seal, such that the housing (found at the top and bottom) encases the filtration membranes.

In the embodiments of FIG. 1, the filter 110 may comprise a waterproof membrane 113, support frame 115, and dustproof membrane 114, all located within the housing. The waterproof membrane 113 may be located downstream (e.g. above) the dustproof membrane 114 in FIG. 1. Additionally, the support frame 115 may be located between the waterproof membrane 113 and the dustproof membrane 114. Typically, the waterproof membrane 113 of FIG. 1 is formed of polytetrafluorethylene (PTFE), and the dustproof membrane 114 of FIG. 1 is formed of polypropylene nonwoven (PPNW). The distance (e.g. gap) between the waterproof membrane 113 and the dustproof membrane 114 may be 1-3, 2-3, 1-5, 2-5, or 3-5 millimeters in FIG. 1, and the dustproof membrane 114 may contact the support frame 115 (for example, with the support frame 115 resting atop and contacting the dustproof membrane 114). The support frame 115 may, in some embodiments, fit snuggly within the bottom housing 112. The support frame 115 of FIG. 1 may comprise one or more airflow apertures, with the airflow apertures of FIG. 1 aligning with the inlet apertures in the bottom housing 112. In some embodiments, the support frame 115 may serve a spacing function between the waterproof membrane 113 and the dustproof membrane 114 (although in FIG. 1, there is a gap between the support frame 115 and the waterproof membrane 113) and/or may be the same diameter as the waterproof membrane 113 and dustproof membrane 114 to snugly fit within the housing.

In FIG. 1, the filter 110 may also comprise a removable splash-proof cap 130 configured to prevent liquid water from communicating with the filter 110. The splash-proof cap 130 may comprise a hollow body 131 with a top opening large enough to fit snuggly onto the bottom housing 112. In FIG. 1, the hollow body 131 is tubular, but it may be of any shape or size in other embodiments (so long as it can attach snugly to the bottom housing 112). Additionally, the splash-proof cap 130 may comprise one or more entry apertures 133 in its bottom end and one or more baffles 132. The entry apertures 133 may communicate with the outside ambient environment and may be operable to allow airflow into the open cavity of the hollow body 131 and into the filter 110. The entry apertures 133 of FIG. 1 typically would have an open surface area at least as great as that of the inlet apertures in the bottom housing 112. In FIG. 1, the entry apertures 133 are typically aligned with the inlet apertures and sized similarly. The baffles 132 may be spaced approximately 3-4 millimeters inward (e.g. inset) from the entry apertures 133 and may prevent water from entering into the hollow body 131. Also, in FIG. 1, the bottom surface 134 may be configured to curve inward with respect to the hollow body 131 to serve a bowl-like function to direct the water blocked by the baffles 132 to drain out of the entry apertures 133.

Figure 2:
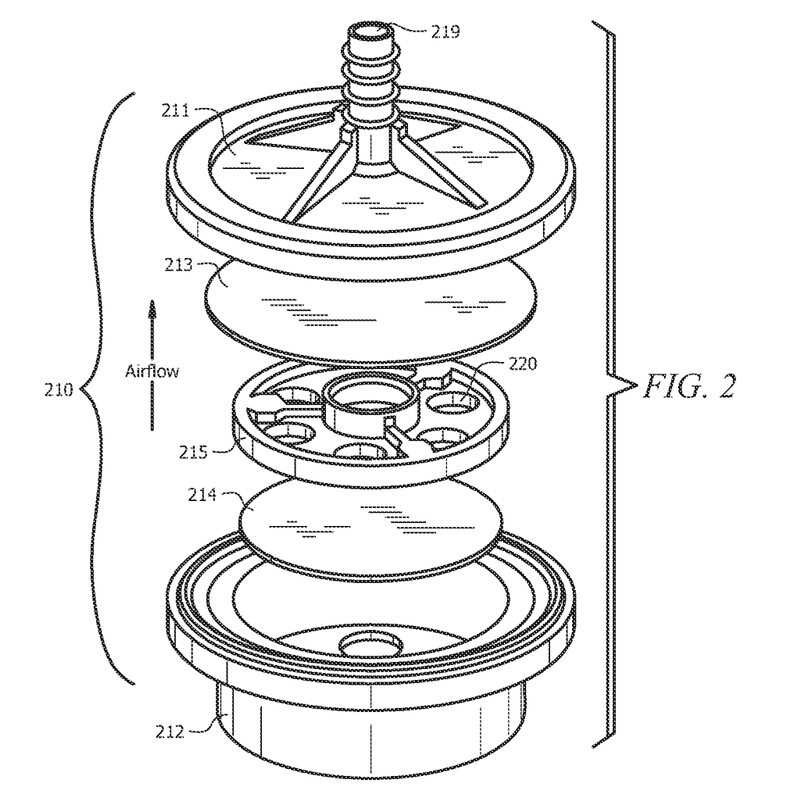
FIG. 2 illustrates an exploded view of an exemplary filter of FIG. 1.
Figure 3:
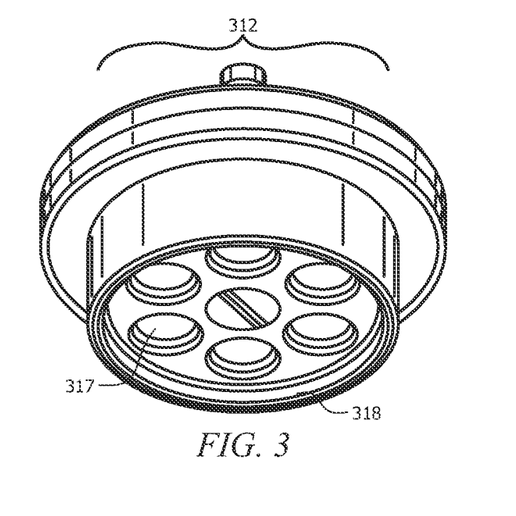
FIG. 3 illustrates a perspective view of a bottom housing of an exemplary filter comprising entry apertures and a raised lip around the perimeter.

FIG. 2 illustrates an exploded view of an exemplary filter 210 of the type shown in FIG. 1 where the filter comprises a top housing 211, water-proof membrane 213, support frame 215, dustproof membrane 214, and bottom housing 212. As discussed in reference to FIG. 1, there may be one or more outlet apertures 219 on the top housing 211 (which could vary in shape and location), but the embodiment of FIG. 1 typically has a single, centrally located outlet aperture 119. In addition, the hollow projection 116 for the outlet aperture 219 may comprise ridges to provide frictional force to snugly hold the gas detector tubing in place. The waterproof membrane 213 of FIG. 2 may be formed of PTFE and may be welded onto the housing via supersonic welding. Typically, the waterproof membrane 213 may have a diameter large enough to fit snugly within the housing. Located upstream of the waterproof membrane 213, there may optionally be a support frame 215. The support frame 215 of FIG. 2 comprises one or more airflow apertures 220 which may align with the inlet apertures in the bottom housing 212 (and in FIG. 1, the airflow apertures are sized similarly to the inlet apertures). In some embodiments, the support frame 215 may be configured to serve a spacing function between the waterproof membrane 213 and the dustproof membrane 214. In other embodiments, the support frame 215 may contact the waterproof membrane 213 and dustproof membrane 214. Typically, the distance between the waterproof membrane 213 and the dustproof membrane 214 may be 1-3, 1-5, 2-3, 2-5, 1-10, or 5-10 millimeters. This distance (e.g. gap) may prolong the service life and efficiency of the filter 210, and may provide sufficient space for any condensing water to exit the housing before saturating through the waterproof membrane 213. Located upstream of the support frame 215, there may be a separate dustproof membrane 214 in FIG. 1. The dustproof membrane 214 may be formed of PPNW and may have a diameter large enough to fit snugly within the housing (but in any case, the dustproof membrane 214 should cover all inlet apertures). Further upstream of the dustproof membrane 214 in FIG. 2, there may be a bottom housing 212 (with the dustproof membrane 214 typically contacting the bottom housing 212). The bottom housing 112 of FIG. 1 comprises a recessed portion extending downward (e.g. upstream) from a rim or flange, and, typically, comprises one or more inlet apertures. In FIG. 1, there are six inlet apertures, and typically, each aperture has a diameter between 6-7 millimeters. Optionally, each of the one or more inlet apertures 317 shown in FIG. 3 may have a raised lip extending around the perimeter. And as shown in FIG. 3, the bottom housing 312 may also comprise a raised lip 318 extending downward (e.g. upstream) around a perimeter of the bottom surface of the bottom housing 312.

Figure 4:
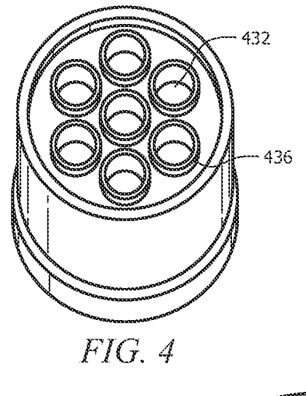
FIG. 4 illustrates a perspective view (from the bottom exterior angle) of a splash-proof cap comprising entry apertures, baffles, and, optionally, raised lips around the perimeter of each aperture.
Figure 5:
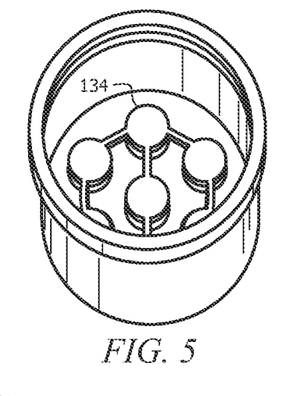
FIG. 5 illustrates a perspective view (from a top interior angle) of a splash-proof cap comprising baffles.

FIGS. 4-5 illustrate a splash-proof cap embodiment 430 (similar to that in FIG. 1) comprising one or more entry apertures 433 and one or more baffles 532, wherein the baffles 532 may be configured to align with the entry apertures 433. In FIG. 4, the bottom of the splash-proof cap 430 comprises seven entry apertures 433, which are typically sized similarly to the inlet apertures (and, typically, in some embodiments, the baffles 534 may be spaced approximately 3-4 millimeters away from the entry aperture 433 and may be located within the hollow body). Additionally, the baffles 532 may be positioned to be parallel to the corresponding entry aperture 433 and may have a surface area at least as large as the corresponding aperture. In other embodiments, the entry apertures 433 may comprise a raised lip 436 extending around the perimeter of each aperture. Also, in some embodiments, the splash-proof cap 430 may comprise a raised lip 435 extending around the perimeter of the bottom surface.

Although in FIG. 4, the number of baffles 532 coincide directly with the number of entry apertures 432, it should be made clear that the number of baffles 532 do not have to be the same as the number of entry apertures 433. For example, one baffle 532 with a larger surface area than the surface area of the entry apertures 433 could be aligned with the entry apertures 433 to prevent water from splashing in.

FIG. 5 better illustrates that the splash-proof cap 530 may have a curved bottom surface. The baffles 532 may be configured to prevent water from splashing in through the entry apertures 433 while also allowing air flow from the surrounding environment. The bottom surface 534 may be configured to curve inward with respect to the hollow body to allow returned water to seep out of the embodiment (via the entry apertures) and back into the surrounding environment.

Figure 6:
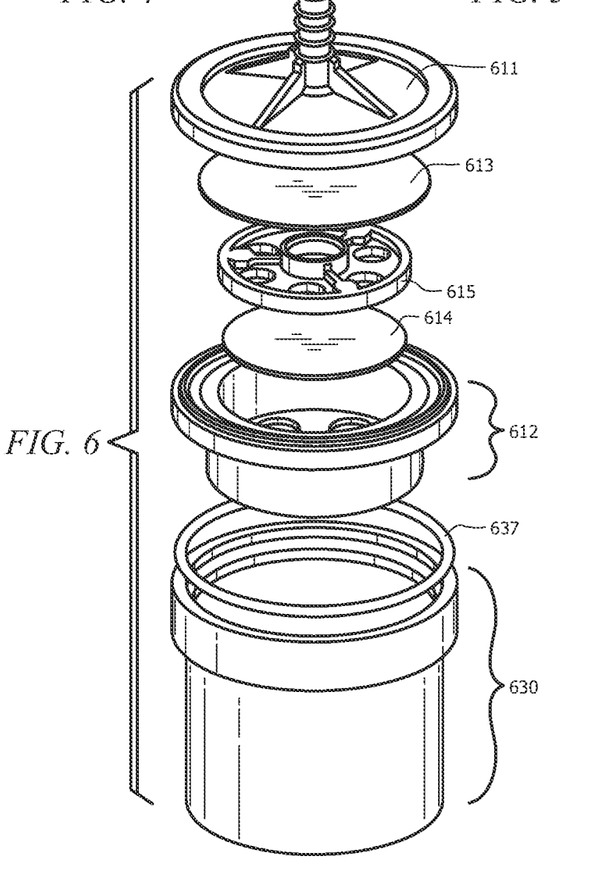
FIG. 6 illustrates an exploded view of an exemplary filter of FIG. 1.

FIG. 6 illustrates an exploded view of the exemplary filter of FIG. 1, further illustrating that the splash-proof cap 630 may have an elastomeric bumper 637. The splash-proof cap 630 may be configured for attachment onto the bottom housing 612. In some embodiments, the splash-proof cap 630 may be configured for removable attachment. For example, as shown in FIG. 6, the splash-proof cap 630 may press-fit onto the bottom housing 612 via the elastomeric bumper 637 (with the elastomeric bumper 637 providing an interference fit that securely holds the splash-proof cap 630 onto the bottom housing 612 and seals the connection). In other embodiments, the splash-proof cap 630 may screw onto the bottom housing 612. Generally, the splash-proof cap 630 may be tubular comprising a hollow body with an open cavity as illustrated in FIG. 6. However, in some embodiments, the splash-proof cap 630 may be of any size or shape as long as the splash-proof cap 630 comprises a hollow body to allow air to communicate with the filter and is configured to snugly fit onto the bottom housing 612. The splash-proof cap hollow body typically has a depth greater than 5 millimeters, for example 5-10 millimeters or 5-15 millimeters.

Figure 7A:
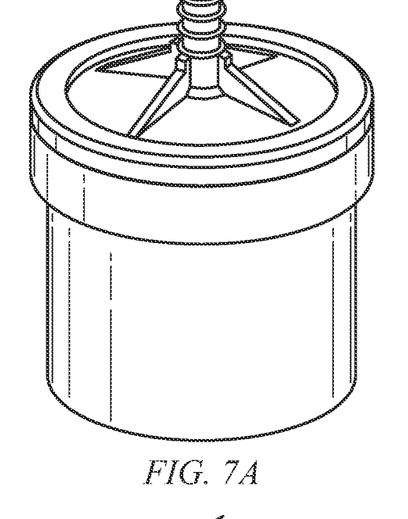
FIG. 7A illustrates a perspective view of an exemplary embodiment of a filter and a splash-proof cap.
Figure 7B:
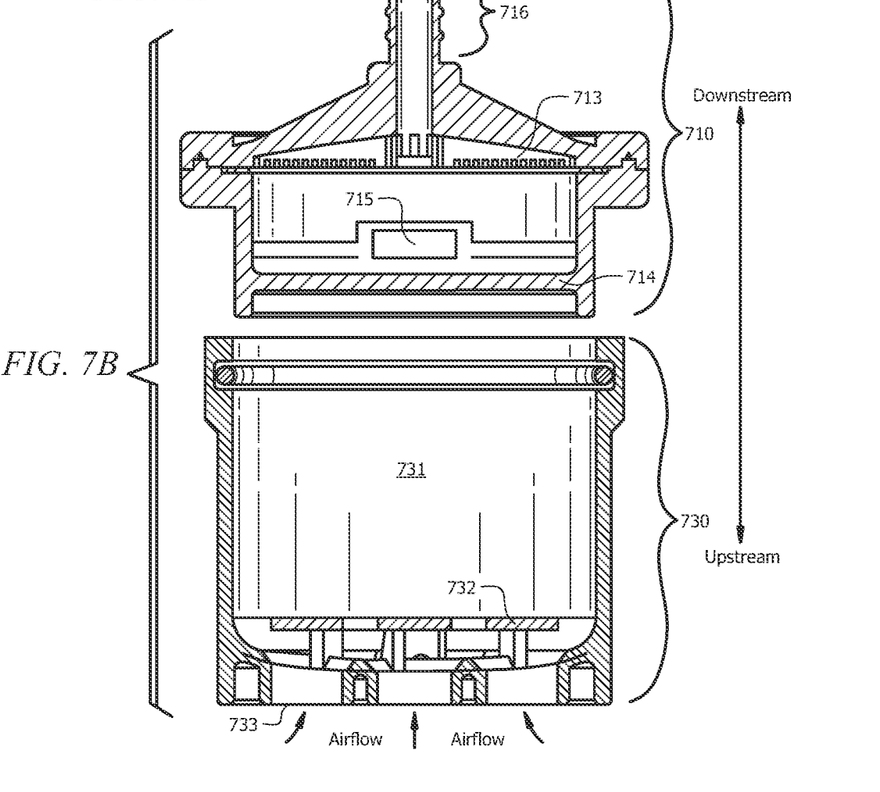
FIG. 7B illustrates a sectional view of an exemplary filter and an exemplary splash-proof cap, wherein the direction of airflow is indicated via arrows.

FIG. 7A illustrates an exterior, perspective view of an exemplary embodiment of a filter with a splash-proof cap. FIG. 7B illustrates a sectional view of an exemplary filter 710 and an exemplary splash-proof cap 730 (similar to FIG. 1), wherein the direction of airflow from the surrounding environment is indicated via arrows. Typically, airflow is induced by the gas sensor attached to the outlet aperture 719, which for example, may pump air through the filter 710 and into the gas pipe (for example, using a fan). Thus, the air from the ambient environment may be drawn in and flow through the entry apertures 733 in the splash-proof cap 730 and may communicate with the baffles 732 which are directly aligned with the entry apertures 733. The air may then travel around the baffles 732, travel through the hollow body 731, travel through the apertures in the bottom housing, permeate through the dustproof membrane 714, travel through the airflow apertures in the support frame 715, permeate through the waterproof membrane 713, exit through the outlet aperture 719, and, lastly, communicate with the gas detector device (for example, via tubing connected to the outlet aperture).

Figure 8:
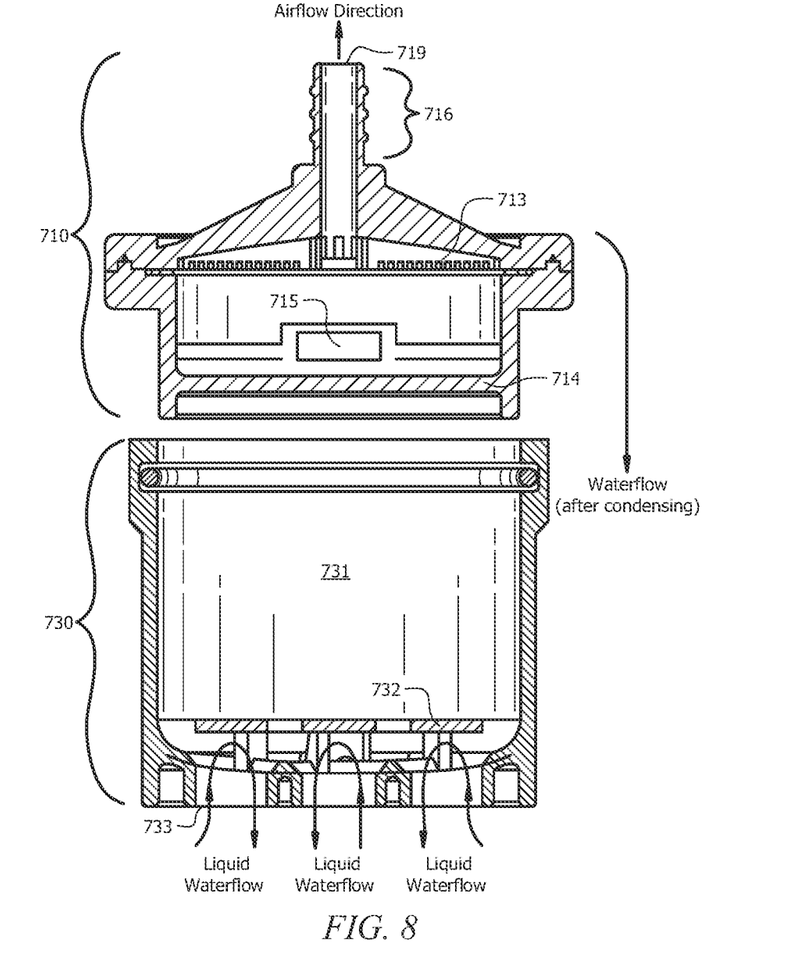
FIG. 8 illustrates a sectional view of an exemplary filter and an exemplary splash-proof cap, wherein the direction of water flow is indicated via arrows.

During the process of airflow through an exemplary embodiment, water may also communicate with an exemplary filter 810 and an exemplary splash-proof cap 830 as shown in FIG. 8. In some cases, humid/moist air may travel through the entry apertures 833, communicate with the baffles 832, travel through the hollow body 831, travel through the inlet apertures, permeate through the dustproof membrane 814, travel through the air flow apertures in the support frame 815, and condense at the waterproof membrane 813. Once the moisture condenses to form water, the water may trickle down into the hollow body 831 and contact the bottom surface of the splash-proof cap 830. Once at the bottom surface (which is configured to be curved inward with respect to the hollow body 831 or otherwise configured to direct water out of the entry apertures 833), the water may exit through the entry apertures 833. In other cases, splashing water from the ambient environment may contact the splash-proof cap 830. In this case, the one or more baffles 832 may prevent any splashes from communicating with the filter 810. The water may enter through the entry apertures 833, hit the baffles 832, and seep/drain to the bottom. Again, the bottom lip is configured to drain the water out of the entry apertures 833. In some cases, the water may not necessarily communicate with the entry apertures 833, but may communicate with the bottom surface of the splash-proof cap 830. In this case, the raised lip around the perimeter of the bottom of the splash-proof cap 830 and/or the raised lip and each entry aperture 833 may block the water so that the water may drop back into the ambient environment.

Having described the devices and methods herein, various embodiments can include, but are not limited to:

In a first embodiment, a filter comprises a top housing, having at least one outlet aperture; a bottom housing, having one or more inlet apertures; a dustproof membrane; and a waterproof membrane. A second embodiment can include the filter of the first embodiment, wherein the dustproof membrane is located upstream of the waterproof membrane. A third embodiment can include the filter of the first or second embodiments, wherein each of the one or more inlet apertures has a diameter of approximately 6-7 square millimeters (and there typically may be 6 such inlet apertures), and wherein the one or more outlet apertures has a diameter of 6 millimeters or less (and, typically, there may be only one such outlet aperture). A fourth embodiment can include the filter of any of the first to third embodiments, wherein the bottom housing comprises a raised lip extending around a perimeter of a bottom surface of the bottom housing. A fifth embodiment can include the filter of any of the first to fourth embodiments, wherein the waterproof membrane is attached to a top surface of the bottom housing by welding. A sixth embodiment can include the filter of any of the first to fifth embodiments, further comprising a support frame located between the dustproof membrane and the waterproof membrane. A seventh embodiment can include the filter of any of the first to sixth embodiments, wherein the support frame comprises one or more air flow apertures, and wherein the one or more air flow apertures correspond with the one or more inlet apertures in the bottom housing. An eighth embodiment can include the filter of any of the first to seventh embodiments, wherein the dustproof membrane is spaced approximately 1-5 (or, alternatively, 1-3, 2-3, 2-5, or 3-5) millimeters from the waterproof membrane. A ninth embodiment can include the filter of any of the first to eighth embodiments, further comprising a splash-proof cap which comprises a hollow body with a top open end configured for attachment onto the bottom housing. A tenth embodiment can include the filter of any of the first to ninth embodiments, further comprising: a bottom surface of the hollow body having one or more entry apertures wherein the bottom surface of the hollow body is curved inward with respect to the hollow body; and one or more baffles corresponding with the one or more entry apertures in the bottom surface. An eleventh embodiment can include the filter of any of the first to tenth embodiments, wherein each of the baffles are aligned with the corresponding entry aperture, wherein each baffle is generally parallel to the corresponding entry aperture, wherein each baffle is sized to be at least as large as the corresponding entry aperture, and wherein the baffles are located within the hollow body of the splash-proof cap and spaced approximately 3-4 millimeters from the corresponding entry aperture. A twelfth embodiment can include the filter of any of the first to eleventh embodiments, wherein the bottom surface of the hollow body of the splash-proof cap comprises a raised lip around the perimeter. A thirteenth embodiment can include the filter of any of the first to twelfth embodiments, wherein the entry apertures of the splash-proof cap further comprise a raised lip around the perimeter of the entry apertures. A fourteenth embodiment can include the filter of any of the first to thirteenth embodiments, wherein the splash-proof cap is removably attached to the bottom housing. A fifteenth embodiment can include the filter of any of the first to fourteenth embodiments, wherein the splash-proof cap further comprises an elastomeric bumper on an inner surface of the hollow body, configured to allow press-fit attachment of the splash-proof cap to the bottom housing. A sixteenth embodiment can include the filter of any of the first to fifteenth embodiments, wherein the dustproof membrane comprises polypropylene nonwoven (PPNW), and wherein the water-proof membrane comprises polytetrafluoroethylene (PTFE). A seventeenth embodiment can include the filter of any of the first to seventeenth embodiments, wherein the ratio of the size of the inlet apertures to the size of the outlet aperture is 6 to 1.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification, and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as "comprises," "includes," and "having" should be understood to provide support for narrower terms such as "consisting of," "consisting essentially of," and "comprised substantially of." Use of the terms "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system, or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An apparatus comprising a splash-proof cap, wherein the splash-proof cap comprises:
    a hollow body with a top open end;
    a bottom surface of the hollow body defining one or more entry apertures, wherein the hollow body of the splash-proof cap comprises a raised lip around a perimeter; and
    one or more baffles corresponding with the one or more entry apertures in the bottom surface.

2. The apparatus according to claim 1, further comprising a filter, wherein the filter further comprises:
    a bottom housing, wherein the top open end of the hollow body of the splash-proof cap is configured for attachment onto the bottom housing of the filter;
    one or more inlet apertures defining 6 inlet apertures each of which define a diameter of 6-7 millimeters; and
    a single outlet aperture having a diameter of 6 millimeters or less, wherein a ratio of a size of the inlet apertures to a size of the single outlet aperture is approximately 6 to 1 or more.

3. The apparatus according to claim 2, wherein the filter further comprises a waterproof membrane attached to a top surface of the bottom housing by welding.

4. The apparatus according to claim 3, wherein the filter further comprises a dustproof membrane.

5. The apparatus according to claim 4, wherein the filter further comprises a support frame located between the dustproof membrane and the waterproof membrane, wherein the support frame comprises one or more air flow apertures, and wherein the one or more air flow apertures correspond with the one or more inlet apertures in the bottom housing.

6. The apparatus according to claim 1, wherein the bottom surface of the hollow body is curved inward with respect to the hollow body.

7. The apparatus according to claim 6, wherein each baffle of the one or more baffles is generally parallel to a corresponding entry aperture, wherein each baffle of the one or more baffles is sized to be at least as large as the corresponding entry aperture, and wherein the one or more baffles are located within the hollow body of the splash-proof cap and spaced approximately 3-4 millimeters from the corresponding entry aperture.

8. The apparatus according to claim 6, wherein each of the one or more entry apertures of the splash-proof cap further comprise a corresponding raised lip around the perimeter of each of the one or more entry apertures.

9. The apparatus according to claim 6, further comprising a filter, wherein the splash-proof cap is removably attached to a bottom housing of the filter.

10. The apparatus according to claim 9, further comprising an elastomeric bumper on an inner surface of the hollow body configured to allow press-fit attachment of the splash-proof cap to the bottom housing of the filter.

11. The apparatus according to claim 4, wherein the dustproof membrane comprises polypropylene nonwoven (PPNW), and wherein the waterproof membrane comprises polytetrafluoroethylene (PTFE).

12. The apparatus of claim 4, wherein the waterproof membrane is located downstream of the dustproof membrane.

13. The apparatus according to claim 12, wherein the filter further comprises:
    a support frame located between the dustproof membrane and the waterproof membrane, wherein the support frame comprises one or more air flow apertures, and wherein the one or more air flow apertures align with the one or more inlet apertures in the bottom housing.

14. The apparatus according to claim 13, wherein the bottom surface of the hollow body is curved inward with respect to the hollow body; and wherein the one or more baffles are aligned with one or more corresponding entry apertures in the bottom surface, wherein each baffle of the one or more baffles is generally parallel to a corresponding entry aperture, wherein each baffle of the one or more baffles is sized to be at least as large as the corresponding entry aperture, and wherein the one or more baffles are located within the hollow body of the splash-proof cap and spaced approximately 3-4 millimeters from the one or more corresponding entry apertures.

15. A splash-proof cap comprising:
    a hollow body with a top open end configured for attachment onto a bottom housing;
    a bottom surface of the hollow body having one or more entry apertures wherein the bottom surface of the hollow body is curved inward with respect to the hollow body; and
    one or more baffles corresponding with the one or more entry apertures in the bottom surface.

* * * * *